United States Patent [19]

Metzler et al.

[11] Patent Number: 5,336,240

[45] Date of Patent: Aug. 9, 1994

[54] BONE-DOWEL ASSEMBLY FOR ANCHORING A SUTURE

[75] Inventors: Richard Metzler, Taufkirchen; Reinhold Schmieding, Olching; Peter M. Schmid, Munich, all of Fed. Rep. of Germany

[73] Assignees: Liebscherkunststofftechnik, Gräfelfing; Arthrex Medizinische Instrumente GmbH, Munich, both of Fed. Rep. of Germany

[21] Appl. No.: 845,156

[22] Filed: Mar. 3, 1992

[30] Foreign Application Priority Data

Mar. 4, 1991 [DE] Fed. Rep. of Germany ....... 4106823

[51] Int. Cl.⁵ .............................................. A61B 17/00
[52] U.S. Cl. ..................................... 606/232; 606/72
[58] Field of Search ................. 411/40, 41, 44, 54; 606/60, 67, 68, 72, 73, 76, 77, 104, 232, 233

[56] References Cited

U.S. PATENT DOCUMENTS

| | | | |
|---|---|---|---|
| 1,808,318 | 6/1931 | Pleister | 411/41 |
| 3,089,377 | 5/1963 | Engstrom | 85/2.4 |
| 3,122,049 | 2/1964 | Dieterich et al. | 411/54 X |
| 3,172,329 | 3/1965 | Setzler | 411/54 X |
| 3,954,345 | 5/1976 | Morris | 403/297 |
| 4,073,212 | 2/1978 | Lerich | 411/54 |
| 4,575,294 | 3/1986 | Mermi et al. | 411/54 X |
| 4,632,100 | 12/1986 | Somers et al. | 606/73 |
| 4,778,468 | 10/1988 | Hunt et al. | 606/73 X |
| 4,870,957 | 10/1989 | Goble et al. | 606/73 |
| 4,898,156 | 2/1990 | Gatturna et al. | 606/72 |
| 4,968,315 | 11/1990 | Gatturna | 606/232 X |
| 5,100,417 | 3/1992 | Cerrer et al. | 606/232 X |
| 5,156,616 | 10/1992 | Meadows et al. | 606/73 X |

FOREIGN PATENT DOCUMENTS

| | | |
|---|---|---|
| 0241240 | 4/1987 | European Pat. Off. . |
| 0340159 | 11/1989 | European Pat. Off. . |
| 2451298 | 5/1976 | Fed. Rep. of Germany . |
| 3223411A1 | 1/1991 | Fed. Rep. of Germany . |
| 2264214 | 10/1975 | France . |
| WO89/01767 | 3/1989 | World Int. Prop. O. . |
| WO89/10096 | 11/1989 | World Int. Prop. O. . |

Primary Examiner—Robert A. Hafer
Assistant Examiner—Brian E. Hanlon
Attorney, Agent, or Firm—Ostrolenk, Faber, Gerb & Soffen

[57] ABSTRACT

A bone dowel assembly for attaching a tissue to a bone includes an approximately cylindrical shank having a continuous borehole which extends axially from a free end of the shank to a second end of the shank, and two slots in the outside surface of the shank which communicate with the borehole and extend from the second end of the shank partially along its length to form reeds or tines which expand radially outwardly when an expansion part is forced into the borehole. The expansion part is conical and includes at least one aperture which extends through the expansion part transversely to the longitudinal axis of the shank. Before insertion into a hole drilled in the bone, the assembly is threaded from the free end of the shank through the borehole, out through one of the slots, past an outside portion of the expansion part, through the aperture, again past an outside portion of the expansion part, through the other slot, and back through the borehole to the free end of the shank. The assembly is then inserted, expansion part first, into the hole in the bone and the suture is pulled, while holding the assembly in place, to force the expansion part into the borehole, causing the reeds to expand radially outwardly and wedge against the sides of the hole in which the assembly is placed. The expansion part and shank may be integrally molded and the connecting zone scored or perforated such that the connection or link between the expansion part and shank is broken when force is applied to pull the expansion part into the borehole.

15 Claims, 2 Drawing Sheets

BONE-DOWEL ASSEMBLY FOR ANCHORING A SUTURE

BACKGROUND OF THE INVENTION

1. Field of the Invention

The invention concerns a bone dowel assembly for anchoring a suture.

2. Description of Related Art

In surgery there is often the need to anchor tissue, for instance muscle or fascia, to a bone. The tissue can be affixed to the bone, for example, by a screw, clamp or nail so that the tissue may again grow on the bone. However, because of the high local pressures exerted by the fasteners, such anchoring frequently entails tissue necrosis.

SUMMARY OF THE INVENTION

A primary objective of the present invention is to direct fastening of a tissue to a bone by providing a dowel assembly which can be inserted into a hole drilled into the bone in order to affix a suture by means of which the tissue can be affixed to the bone.

In order to acheive this objective, the bone dowel assembly of the invention includes an approximately cylindrical shank with a continuous borehole extending the axial length of the shank and at least two longitudinal slots in communication with the borehole. The two slots extend as far as one end of the shank, but only over part of the axial length of the shank. The slots are open at the end of the shank to which they extend.

To anchor the dowel assembly of the invention in a bone, a hole is drilled in the bone. The diameter of the hole is such that the bone dowel assembly of the invention, i.e. the dowel shank, can be inserted as a snug fit into this hole. The shank of the bone dowel of the invention includes, at the end which is inserted into the hole drilled into the bone, an expansion part in the approximate shape of a pin. The dowel shank and the expansion part share the same longitudinal axis. In other words, the longitudinal axis of the dowel body and that of the expansion part coincide.

The expansion part is inserted and anchored into the continuous axial borehole in the shank such that an end of the expansion part points toward that end of the dowel body to which the longitudinal slots extend. When the assembly is anchored in the bone, the expansion part extends slightly into the axial borehole of the dowel shank, at which time the dowel shank and the expansion part constitute two mutually separate pieces. However, prior to insertion of the expansion part into the borehole, the expansion part and dowel shank may form a single integrally-molded member.

Anchoring of the assembly to the bone occurs when a force exceeding a given value is exerted on the expansion part in the direction of the longitudinal axis and toward the dowel shank, the expansion part is pulled into the borehole and hence into the dowel shank, causing the shank to expand so that the shank is wedged in place in the hole drilled in the bone.

This force is transmitted by the surgeon using a suture inserted into the free end of the dowel body. The suture is passed through the borehole and exits from one of the slots, passing through a drilled aperture located, in particular, at the free end of the expansion part, the drilled aperture extending transversely to the longitudinal axis of the shank. The suture then returns to the borehole through the second slot and exits again from the free end of the dowel shank. By simultaneously pulling on the suture segments at the free ends of the dowel shank, the suture is tensioned and, when a sufficiently large tension is applied, pulls the expansion part into the borehole of the dowel shank, which in turn is expanded in this zone. During this process, the surgeon must hold the dowel shank in place using a suitable instrument to prevent the bone dowel assembly, while it is only loosely inserted into the bone, from being pulled out as tension is applied to the suture.

The cross-sections of the borehole and of the pin-shaped expansion part in principle may be arbitrary, for instance polygonal, although the cross-sections of the axial borehole and of the expansion part should be surface-congruent at some point along the length of the expansion part, as explained below. The cross-section of the expansion part preferably continuously increases, beginning at the end inserted into the dowel shank, in order to sufficiently expand the dowel shank as the expansion part is pulled into the borehole.

Once the expansion part has been pulled into the dowel shank, the dowel shank is anchored in a stationary manner in the hole made in the bone. Tissue can then be affixed to the bone by means of the suture segments leading out of the dowel assembly, for instance by sewing or tying the tissues to the bone.

In a preferred embodiment of the invention, the axially extending borehole in the dowel shank has a circular cross-section constant over the axial length of the dowel body, and the expansion part represents a cone. Accordingly the cross-sectional area of the expansion part is a circle or a circular surface. The radius of the circle or circular surface increases continuously from the end of the expansion cone inserted into the borehole of the dowel shank toward the free end of the expansion cone. In this manner, especially pronounced expansion is achieved.

The expansion cone should have a diameter at its free end which is slightly smaller than the diameter of the free end of the shank because the suture passes on both sides of the expansion cone before passing through the aperture and some space is required to permit the suture to clear the walls of hole in the bone as the suture passes the expansion part. The free-end diameter of the expansion cone therefore should be less than the free-end diameter of the dowel shank by an amount approximately equal to twice the suture diameter.

In another preferred embodiment of the invention, the inside diameter of the shank borehole at the end receiving the expansion cone is approximately the same as the outside diameter of the expansion cone at the end of the cone which is inserted into the borehole. In other words, the outer surface of the expansion cone should be approximately tangent to the inside surface of the borehole. The expansion cone therefore is inserted into the borehole only to such a depth that its axial alignment and anchoring is ensured.

In yet another preferred embodiment of the invention, the bone dowel assembly including the dowel shank and the expansion cone are integrally injection-molded. The link from the outer surface of the expansion cone, in the zone where it is inserted into the dowel body, to the inside surface of the borehole in this case represents a rupture zone, which may for example be scored or perforated to break in a predetermined manner when the expansion cone is pulled by means of the suture with appropriate force into the dowel shank borehole.

In this embodiment, the outside surface of the expansion cone may coincide in the region of overlap with the inside surface of the borehole, or be tangent to it. However a ring may also be present at this transition between the inside surface of the borehole and the outside surface of the expansion cone, the ring being integral both with the dowel shank and with the expansion cone.

The bone dowel assembly of the invention may be made of any human or animal compatible material, for instance a polycarbonate, depending on the context in which the assembly is used. Preferably, the bone dowel assembly of the invention is made of a material which is absorbable in vivo, such as polylactate, polylactide, or PDS. The suture preferably is also made of an absorbable material. Such sutures are widely known. If the bone dowel assembly and/or the suture are made of an absorbable material, then they will dissolve after some time. As the tissue grows and becomes anchored to the bone, the anchoring means for affixing the tissue to the bone will become superfluous.

BRIEF DESCRIPTION OF THE DRAWINGS

The bone dowel of the invention is elucidated below in relation to the Figures showing sketches of a preferred embodiment.

DETAILED DESCRIPTION OF THE PREFERRED EMBODIMENTS

Figure 1:
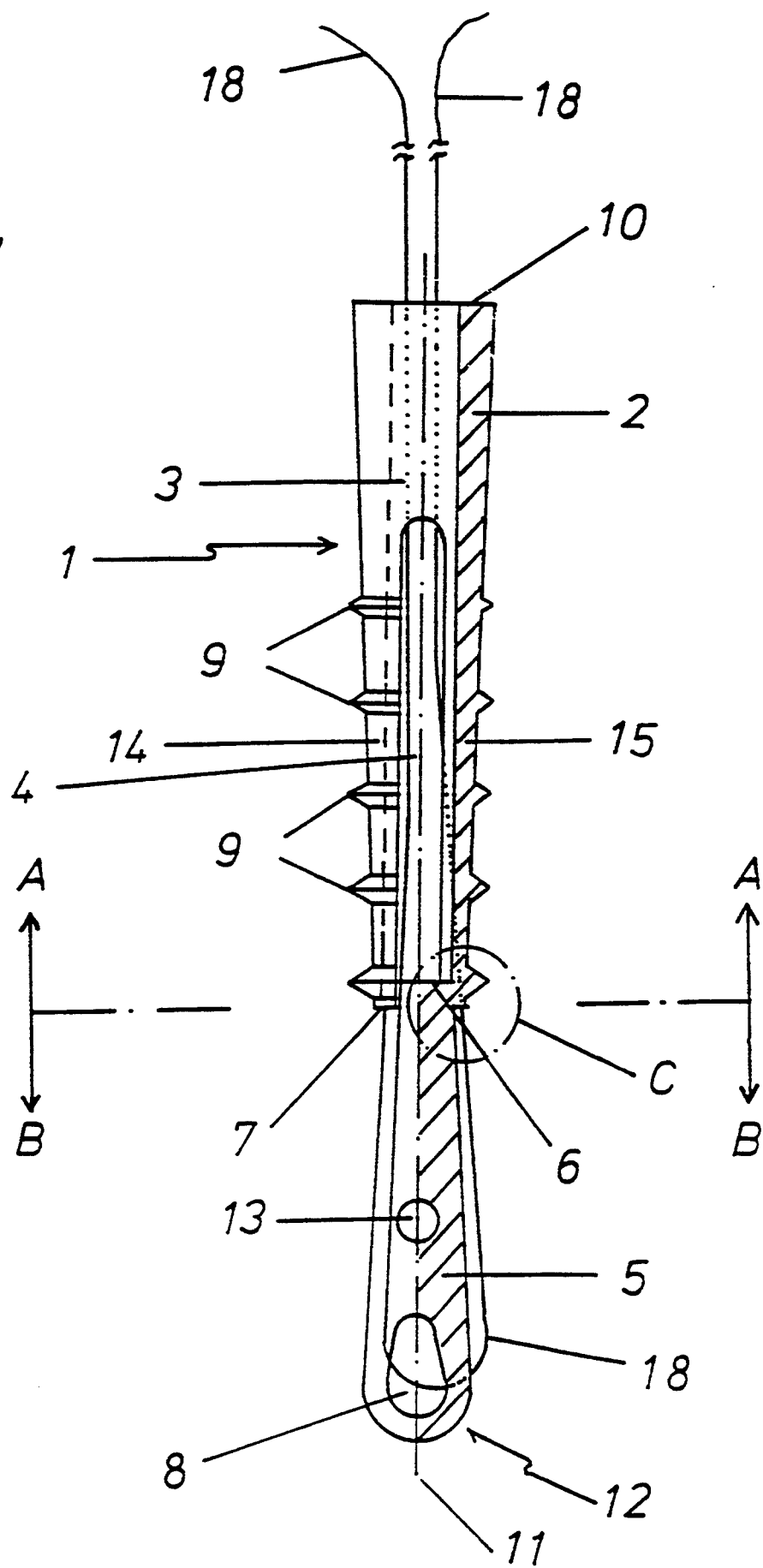
FIG. 1 is a side view in partial section of a bone dowel of the invention.

The bone dowel assembly 1 shown in FIG. 1 includes an approximately cylindrical shank 2 and an expansion cone 5. Shank 2 preferably has a circular cross-section, the radius of which continuously decreases from the free end 10 of the shank to the end 7, although the shank may also have other shapes. In the illustrated embodiment, the approximately cylindrical shank tapers conically toward end 7 and expansion cone 5.

Shank 2 includes a central and continuous axially extending borehole 3 having a circular cross-section which is constant over the axial length of the shank. Starting from the end 7 of shank 2, two diametrically opposite longitudinal slots 4 extend along the side of the shank to beyond the middle of the shank. The slots communicate with the borehole 3 to form two separate mutually opposite tines or reeds 14, 15. Several ribs 9 are present on reeds 14, 15 and extend circumferentially around the periphery of shank 2, their outside diameters corresponding approximately to the shank diameter at its free end 10. Because shank 2 tapers conically toward its end 7, the inside diameter of the circumferential, and hence circularly-arrayed, ribs increases from the end 7 towards the middle of the shank at the base of reeds 14, 15 where slots 4 terminate. In other words, the rib 9 nearest the end 7 is thickest, and this thickness decreases in the direction of the end 10.

End 6 of an expansion part, illustrated as being in the form of an expansion cone 5, is inserted into the end 7 of the dowel shank 2, i.e., into the borehole 3, to anchor the shank in a drilled hole in a bone by causing reeds 14, 15 to expand outwardly against the wall of the drilled hole. At this time, the exemplary expansion cone extends a short distance into the borehole 3.

Figure 4:
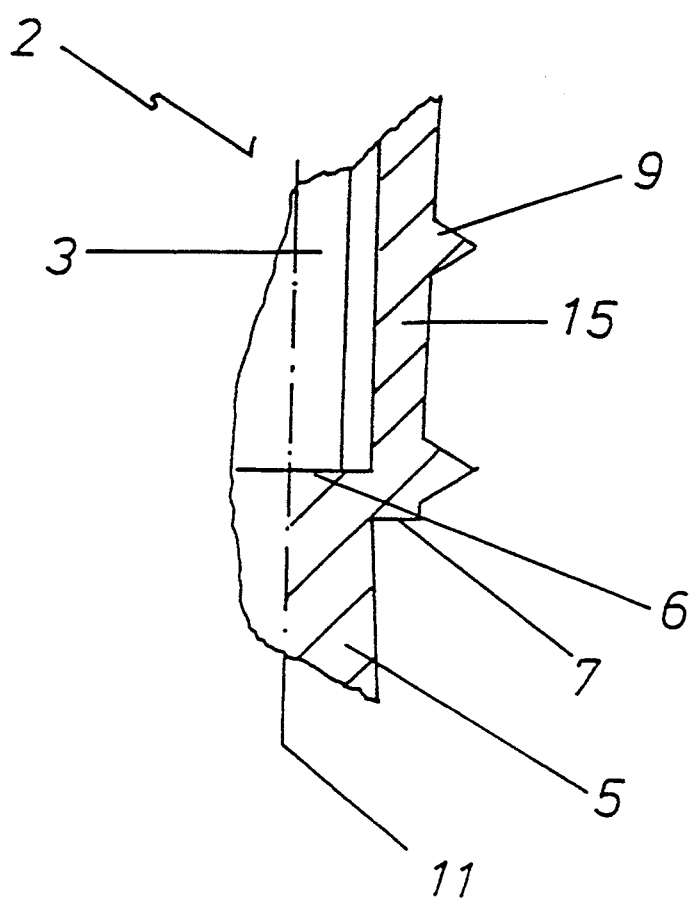
FIG. 4 is an enlargement of a portion of the section shown in FIG. 3.

The dowel shank 2 and the expansion cone 5, according to the illustrated embodiment of the invention, are manufactured as an integral unit by injection molding. As shown in particular by FIG. 4, the expansion cone merges into the dowel shank in the zone where the expansion cone and dowel shank overlap. The outside surface of the expansion cone and the inside surface of borehole 3 of the dowel shank are, however, preferably approximately congruent, and therefore a step is formed as shown at the point of merging.

To use the bone dowel assembly 1, it is inserted, with the expansion cone 5 in front, into a hole or borehole previously made in a bone. The bone hole should be deep enough to fully receive the bone dowel of the invention.

Before insertion, a suture 18 is introduced into the bone dowel assembly of the invention. Suture 18 is inserted at the free end 10 into borehole 3 and from there extends through one of the longitudinal slots 4, from which the suture exits in a direction which is still substantially parallel to the longitudinal axis 11 and then is guided along the outside surface of expansion cone 5 as far as aperture 8 in the expansion cone. The suture is threaded through aperture 8 and then is guided back to the longitudinal slot 4 which is diametrically opposite the first-mentioned longitudinal slot 4, at which point the suture re-enters the borehole 3 and exits from the free end 10.

By simultaneously pulling on the suture segments exiting from the dowel shank 2 at the free end 10, suture 18 is tensioned against an edge or wall of aperture 8 and thereby exerts a force on the expansion cone 5 in the direction of the longitudinal axis 11 towards shank 2. When this force exceeds a specified value, the link between the expansion cone 5 and the dowel shank 2, i.e., the point at which expansion cone 5 and shank 2 are merged, breaks, and the expansion cone 5 is pulled into the borehole 3 of the dowel body 2, causing reeds 14 and 15 to expand and hence be anchored in the hole previously made in the bone. The dowel body at the same time must, of course, be kept pressed into the hole against the force caused by pulling the suture so that the dowel assembly as a whole shall not be pulled out until it is firmly anchored in the bone.

To facilitate breakage of the link between the expansion cone 5 and dowel shank 2, a scored or perforated rupture zone is formed. The force which must be applied for the desired break to take place at this scored rupture zone is determined, among other factors, by the length by which the expansion cone 5 is to extend into the borehole 3. The larger the overlap zone, the larger the force which must be applied in order to break the material at this site. Upon breakage of the rupture zone, the ends of tines 14 and 15 are free to expand outwardly in response to insertion of the expansion cone.

The axial length of the expansion cone preferably corresponds approximately to the axial length of the longitudinal slots 4 in order to provide maximum expansion of reeds 14 and 15.

The drilled aperture 8 in expansion cone 5 preferably has an oval or pear shape, the long axis of the oval or pear shape coinciding with the longitudinal axis 11 of the bone dowel. The wall of the aperture 8 is arcuate in the zone pointing toward the end 6 of the expansion cone 5 so that the suture 18, without being snagged, can still be moved or pulled by the surgeon, if necessary, even after the expansion cone 5 has been drawn into borehole 3 of the shank 2. The wall zone being rounded, the suture 18 does not catch or jam at edges of the hole.

The expansion cone 5 also includes another continuous aperture 13 present between the aperture 8 and the end 6 of the expansion cone, extending perpendicular to longitudinal axis 11. This second continuous aperture 13 in the expansion cone is strictly cylindrical and as a result has a sharp edge at the transition to the outside surface of the expansion cone 5. If the suture 18 is made to pass through this second aperture 13, and therefore not through the aperture 8 as shown in FIG. 1, then the suture 18 will be bent nearly perpendicularly at the edge of the second aperture 13 and no longer can be pulled through. Thus, depending on whether the suture is to be moved with respect to the bone, or firmly affixed therein, the suture 18 may be made to pass through the second aperture 13 or through the first aperture 8. The second aperture 13 should have a diameter corresponding approximately to that of the suture, while the diameter of the aperture 8 should be larger than that of the suture 18.

Figure 2:
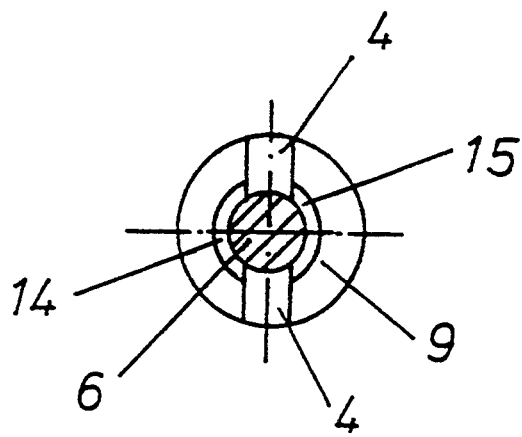
FIG. 2 is a section along line A—A of FIG. 1.
Figure 3:
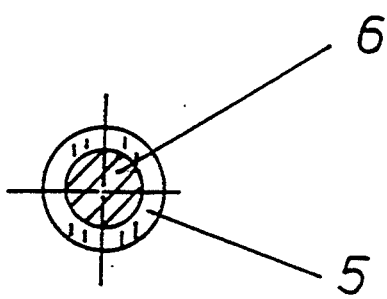
FIG. 3 is a section along line B—B of FIG. 1.

As shown in particular by FIG. 3, the expansion cone 5 tapers towards the end 6 which is inserted into borehole 3 of shank 2. The section A—A shown in FIG. 2 makes especially clear that the longitudinal slots 4 are diametrically opposite each other and pass between two reeds 14 and 15, and that they are open at the end 7 of shank 2.

The center lines of the longitudinal slots 4 and the longitudinal axes of the apertures 8 and 13 are in a first plane which is perpendicular to a second plane, slots 4 being spaced from and parallel to the second plane. The longitudinal axis 11 lies in the second plane and also in the first plane, but is perpendicular to the longitudinal axes of apertures 8 and 13. This design assures that the expansion cone 5 can be fully pulled into the dowel body, and even deeper, without the reeds 14 and 15 covering the apertures 8, 13 and thereby clamping the suture 18, which would prevent the suture from being pulled sufficiently to completely wedge cone 5 into borehole 3. Accordingly the width of the longitudinal slots 4 preferably corresponds approximately to the diameter of the drilled apertures 8 and 13.

The bone dowel assembly of the invention is preferably injection-molded of a material which is absorbable in vivo, for instance polylactate, polylactide, or PDS, so that the assembly will eventually vanish as the tissue and the bone to which it is attached grow together.

Having thus described a specific preferred embodiment of the invention, as illustrated in the drawings, it should nevertheless be appreciated that the invention is intended to cover not only the specific embodiment described and shown herein, but also all other variations which will occur to those skilled in the art based on the disclosure of the invention, and which are covered by the appended claims. For example, the expansion part need not be cone shaped, nor it is required to be integrally molded with the dowel shank. Similar, as noted above, the shank borehole does not need to be strictly cylindrical, so long as the assembly can be inserted into a hole in a bone and easily wedged therein by pulling of a suture which is threaded through the shank and the expansion part.

We claim:

1. A suture-anchoring bone dowel assembly, comprising:
    an approximately cylindrical dowel shank made of a material which is absorbable in vivo having two ends connected by a central longitudinal axis and including a borehole extending from a free end of the shank to a second end of the shank along the longitudinal axis, said shank also including at least two longitudinal slots in communication with the borehole, said slots being open at said second end of the shank and extending along a portion of the shank; and
    an approximately pin-shaped expansion part made of a material which is absorbable in vivo having two ends connected by a second longitudinal axis coincident with that of the shank, and means defining at least one aperture extending approximately perpendicular to the second longitudinal axis for receiving a suture by which a force exceeding a predetermined value is applied to the expansion part,
    wherein said expansion part is arranged to be pulled into the borehole at the second end of the shank when said force exceeding predetermined value is applied to the expansion part in a direction parallel to said longitudinal axes, said direction being towards the shank, thereby causing the shank to expand and become wedged against walls of a hole in a bone into which the assembly is inserted.

2. An assembly as claimed in claim 1, wherein the borehole has a constant circular cross-section along an axial length of the shank.

3. An assembly as claimed in claim 1, wherein the expansion part is a cone-shaped expansion cone.

4. An assembly as claimed in claim 3, wherein an inside diameter of the borehole at said second end of the shank is approximately equal to an outside diameter of the expansion cone at an end which is arranged to be pulled into the borehole.

5. An assembly as claimed in claim 3, wherein the shank and the expansion cone are integrally injection molded together.

6. An assembly as claimed in claim 5, wherein a link from the outside surface of the expansion cone, in a zone where the expansion cone is arranged to extend into the shank, to the inside surface of the borehole, is a rupture zone arranged to break when said force is applied to said expansion part to cause it to be pulled into said borehole.

7. As assembly as claimed in claim 1, wherein said material is polylactate.

8. An assembly as claimed in claim 1, wherein an outside diameter of the shank continuously decreases from said free end to said second end.

9. An assembly as claimed in claim 1, further comprising a plurality of axially spaced ribs located on a portion of the shank which includes the longitudinal slots and extending around a periphery of the shank, an outside diameter of the ribs approximately equalling an outside diameter of the free end of the shank.

10. An assembly as claimed in claim 1, wherein said aperture has an oval or pear shape of which a long axis coincides with the longitudinal axis of the shank, wherein the aperture is located at a free end of the expansion part opposite a second end of the expansion part which is arranged to extend into the borehole, and wherein a wall of the aperture nearest the second end of the expansion part is arcuate.

11. An assembly as claimed in claim 10, further comprising a second aperture extending transverse to the longitudinal axis of the expansion part and having a constant, circular cross-section, said second aperture being located in said expansion part between the first aperture and said second end of the expansion part.

12. An assembly as claimed in claim 11, wherein central lines of the longitudinal slots and longitudinal axes of the first and second apertures are located in a plane in which the longitudinal axis of said expansion part is also located.

13. An assembly as claimed in claim 12, wherein an axial length of the longitudinal slots is approximately equal to an axial length of the expansion cone.

14. An assembly as claimed in claim 12, wherein said borehole, said longitudinal slots, and said first aperture form a path for threading a suture, beginning at the free end of the shank and passing through, in order, the borehole, a first of said longitudinal slots, an outside surface of the expansion part between the expansion part and the walls of the bone hole, the first aperture, a second of said longitudinal slots, and again the borehole, such that when the suture is pulled, tension is applied against a wall of the first aperture and therefore against the expansion part to cause the expansion part to enter the borehole and thereby cause the shank to expand against the walls of the bone hole.

15. An assembly as claimed in claim 1, wherein said borehole, said longitudinal slots, and said aperture form a path for threading a suture, beginning at the free end of the shank and passing through, in order, the borehole, a first of said longitudinal slots, an outside surface of the expansion part between the expansion part and the walls of the bone hole, the aperture, a second of said longitudinal slots, and again the borehole, such that when the suture is pulled, tension is applied against a wall of the aperture and therefore against the expansion part to cause the expansion part to enter the borehole and thereby cause the shank to expand against the walls of the bone hole.

* * * * *